United States Patent [19]

Kondo et al.

[11] Patent Number: 4,572,201
[45] Date of Patent: Feb. 25, 1986

[54] PROBE FOR INTRALUMINAL ULTRASONIC SCANNER

[75] Inventors: Shinichi Kondo, Hachioji; Chitose Nakaya, Nishitama; Shizuo Ishikawa, Tsukui, all of Japan

[73] Assignee: Hitachi, Ltd., Tokyo, Japan

[21] Appl. No.: 659,672

[22] Filed: Oct. 11, 1984

[30] Foreign Application Priority Data

Oct. 11, 1983 [JP] Japan .................. 58-189694

[51] Int. Cl.⁴ .............................. A61B 10/00
[52] U.S. Cl. .......................... 128/660; 128/4; 73/623
[58] Field of Search .................. 128/660, 4; 73/619–620, 623, 625–626

[56] References Cited

U.S. PATENT DOCUMENTS

| 4,248,090 | 2/1981 | Glenn | 128/660 X |
| 4,398,422 | 8/1983 | Haerten | 128/660 X |
| 4,431,006 | 2/1984 | Trimmer et al. | 128/660 |

Primary Examiner—Kyle L. Howell
Assistant Examiner—Francis J. Jaworski
Attorney, Agent, or Firm—Antonelli, Terry & Wands

[57] ABSTRACT

A probe which is inserted into a lumen to obtain an ultrasonic tomogram using mechanical scanning is disclosed. A cylindrical acoustic case is filled with a liquid medium which transmits sound waves, and an elliptical ultrasonic transducer is immersed therein in such a manner that it can be rotated by a motor. The diameter of the transducer parallel to its axis of rotation is greater than that perpendicular to the axis of rotation, so that the lateral resolution parallel to the axis of rotation is improved, as well as the sensitivity.

4 Claims, 5 Drawing Figures

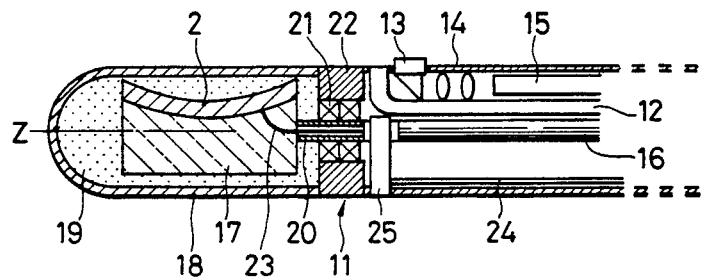
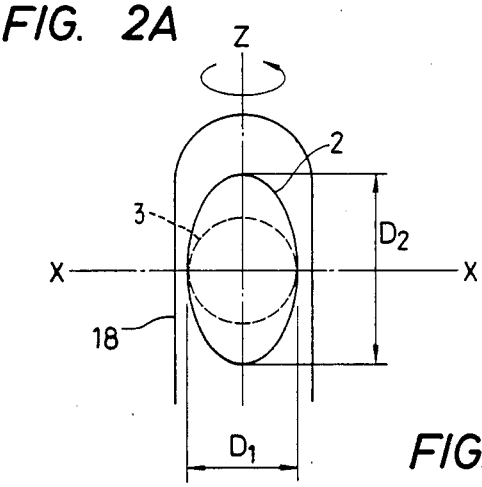
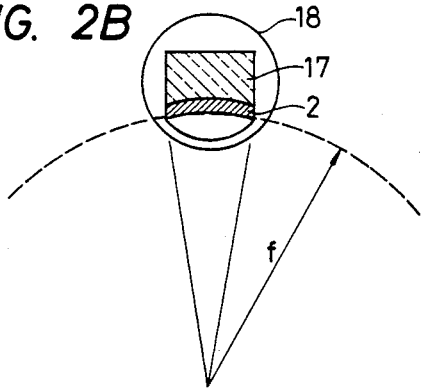

PROBE FOR INTRALUMINAL ULTRASONIC SCANNER

BACKGROUND OF THE INVENTION

1. Field of the Invention

This invention relates to a probe for an intraluminal ultrasonic scanner, and more particularly to a probe which is inserted into a lumen of a patient so that a transducer therein can scan to provide an ultrasonic tomography of the patient.

2. Description of the Prior Art

Most conventional ultrasonic tomographs are obtained by rediating ultrasonic pulses into the body from the body surface, and by receiving the reflected waves therefrom to obtain information on the inside of the body. Recently, intraluminal tomography in which an ultrasonic probe is inserted into a body cavity and ultrasonic pulses are transmitted to and received from near the organs in a living body has been drawing increasing attention. This method of intraluminal tomography is characterized in that a higher resolution with high frequencies can be obtained because there is less damping of sound waves due to subcutaneous fat layers between the target organ and the probe.

Transrectal tomography is particularly effective for diagnosis related to the prostate, and various apparatuses for this tomography have been proposed in the past. On the other hand, various proposals have also been made for an apparatus for diagnosis concerning the walls of the stomach, the pancreas, and the like, that is, a so-called "echo endoscope". Japanese Patent Laid-Open No. 1984/1979, for example, discloses an apparatus in which a fiber scope and a ultrasonic transducer are assembled into a single probe, and which enables both observation of the surfaces of internal walls and tomography within those walls.

The most ordinary type of this intraluminal ultrasonic scanner is one in which a transducer is mechanically rotated within a probe to obtain a radial tomogram. A problem encountered in this mechanical scanning transducer concerns the size and shape of the transducer. In the prior art in the Japanese Patent Laid-Open document quoted above, a round transducer is used, but there is a limit on the inner diameter of the probe. The lateral resolution in ultrasonic tomography is inversely proportional to the diameter of the transducer, and hence the resolution drops if the diameter of the round transducer is reduced, such as in the prior art described above. In addition, since the sensitivity of the probe is substantially proportional to the sound-wave transmission and reception area of the transducer, the sensitivity drops and the depth that can be observed is less if the diameter of the round transducer is reduced.

SUMMARY OF THE INVENTION

With the background described above, the present invention is directed to providing a probe which can eliminate the problems in the prior art, and which can improve the resolution in the thickness direction of the sectional surface, that is, in the direction parallel to the axis of rotation thereof, as well as the sensitivity.

In a probe element constituted in such a manner that it is rotated mechanically within a probe inserted into a lumen of a patient, the object of the present invention can be accomplished by a probe which is characterized in that the length of a transducer surface in the direction parallel to the axis of rotation thereof is made greater than its length in directions perpendicular to the axis of rotation, so that the resolution in the direction parallel to the axis of rotation is improved, as well as the sensitivity, by the consequent increase in area.

BRIEF DESCRIPTION OF THE DRAWINGS

FIG. 1 is a section through a probe in accordance with one embodiment of the present invention;

FIGS. 2A and 2B are a plan view and a sectioned view of the principal portions of the probe of FIG. 1, respectively;

DESCRIPTION OF THE PREFERRED EMBODIMENTS

Figure 3:
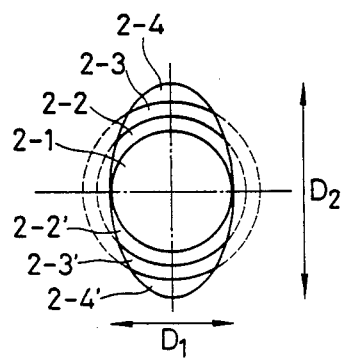
FIG. 3 is a plan view of the probe in accordance with another embodiment of the present invention.

FIG. 1 is a section through the probe tip of a so-called "echo endoscope" used for diagnosis related to the walls of the stomach, the pancreas, and so forth. In this embodiment, both the echo endoscope and a fiber scope are provided in a probe which is inserted into the body through the gullet. In the drawing, reference numeral 12 denotes a light guide for guiding the illumination light, 13 denotes a rectangular prism, 14 an imaging lens, and 15 an image guide. In this optical system, the rectangular prism 13 and the imaging lens 14, which are arranged adjacent to each other in the proximity of a radiating end 12A of the light guide 12, constitute an image formation system which forms an image on the end surface of the image guide 15, and the image thus formed is observed by an external optical system provided for image observation.

Reference numerals 2 and 16 through 25 denote the principal constituents of the echo endoscope. A concave ultrasonic transducer 2 is fixed to a rotary shaft 20 together with a damper member 17 which absorbs sound waves, and is connected to an external motor by a flexible shaft 16. Reference numeral 18 denotes an acoustic case of cylindrical shape which acoustically couples an ultrasonic-wave transmission medium 19 such as olive oil with the patient's body, 21 denotes a support, 22 a bearing, 23 a signal line on the rotational side, 24 a signal line on the fixed side, and 25 a slip ring.

The ultrasonic transducer 2 is driven by pulses from a driving circuit, not shown, through the signal line 24, the slip ring 25, and the signal line 23. The reflected waves generated by this are detected by the transducer, and a detection signal is supplied to a reception circuit back along the route described above. This operation above is repeated as the transducer 2 is rotated by the motor, not shown, centered on the Z-axis, and a tomogram perpendicular to the Z-axis can be obtained thereby.

FIG. 2A is a plan view of just the transducer 2 portion of the probe shown in FIG. 1. As shown in this drawing, the transducer 2 is elliptical. When compared with a conventional transducer 13, represented by dashed line for reference, the transducer 2 of the present invention has the same dimension ($D_1$) perpendicular to the axis of rotation (Z-axis), but has a much larger dimension ($D_2$) parallel to the Z-axis than that of the conventional transducer.

FIG. 2B is a section taken along the line X—X of FIG. 2A. As illustrated in the drawing, the surface of the transducer 2 forms part of a spherical surface of a radius f.

According to Rayleigh, both the lateral resolution (hereinafter called simply "resolution") in the X-axis direction at a distance y and the Z-axis resolution are given by:

$$\Delta = 1.22 \ (\lambda/D)_y$$

where D is the diameter of the transducer.
In this embodiment:
$D = D_1$ in the X-axis direction,
$D = D_2$ in the Z-axis direction, and
$D_1 < D_2$.
Therefore, the following relationships hold, where $\Delta_1$ and $\Delta_2$ are the resolutions in the X-axis direction and the Z-axis direction, respectively:

$$\Delta_1 = 1.22 \ (\lambda/D_1)_y$$

$$\Delta_2 = 1.22 \ (\lambda/D_2)_y$$

In the conventional transducer, the diameter D is $D = D_1$ in both the X- and Z-axis directions, and hence the resolution is $\Delta_1$ in both directions. Therefore, compared with that of the conventional transducer, the resolution of the transducer of this embodiment in the X-axis direction is unchanged, but the resolution in the Z-axis direction can be improved.

As described above, the transducer of this embodiment is provided with a spherical cross-sectional shape in order to utilize the space within the inner surface of the cylindrical acoustic case as effectively as possible. The best shape for this purpose is as follows. The major axis $D_2$ of the ellipse should satisfy the following relationship:

$$D_2 = 2\sqrt{f^2 - (a - r)^2}$$

where f is the focal distance of the concave transducer, $r = R - \delta r$ where R is the inner radius of the acoustic case, and $\delta r$ is the clearance which enables the transducer to rotate smoothly within the acoustic case, with the proviso that $$a = \sqrt{f^2 + r^2 - \frac{D_1^2}{2} + \sqrt{\left(f^2 - \frac{D_1^2}{2}\right)\left(r^2 - \frac{D_1^2}{2}\right)}}$$

The formulae given above determine the common portion of the sphere of radius f and the cylinder of radius r, and a corresponds to the distance between the axis of rotation and the focal point with respect to the minor diameter $D_1$ of the concave transducer.

Although the transducer of the embodiment described above is elliptical, the shape is not particularly limited thereto. For instance, the same results can be obtained using a rectangular transducer which is elongated along the axis of rotation. It is also obvious that a planar transducer can be used in combination with an acoustic lens instead of the concave transducer. When a planar transducer is used, the shape of the transducer is most preferably rectangular, to provide the most effective utilization of the internal space of the cylindrical acoustic case.

It is also possible to employ a multi-ring transducer consisting of a plurality of transducers split in a ring-shaped manner to provide phase differences, so as to synthesize an ultrasonic beam and form a focus. Such an embodiment is illustrated in FIG. 3. The elliptical transducer is divided in a ring-shaped manner into a plurality of elements 2-1, 2-2, 2-3, 2-4, 2-2', 2-3' and 2-4'. The elements are arranged in such a fashion that the elements corresponding to one another vertically, that is, elements 2-2 and 2-2', 2-3 and 2-3', or 2-4 and 2-4', have the same phase. Ultrasonic waves are transmitted and received by controlling the phase of each element pair by changing the focus and the depth direction (y direction). In other words, this arrangement makes it possible to obtain multi-stage focusing, and improve the resolution over a wider range than that of the embodiment of FIGS. 2A and 2B.

Figure 4:
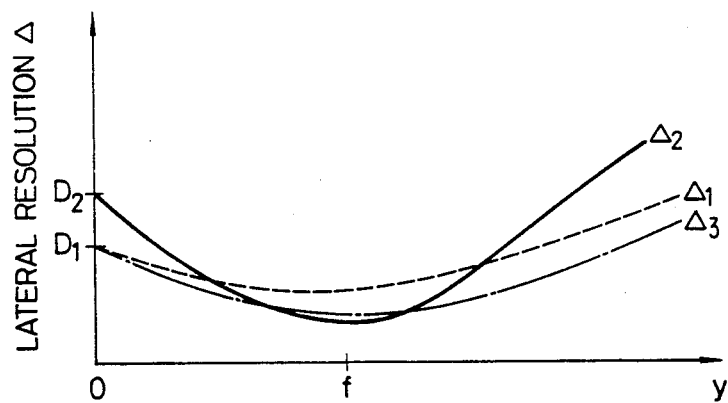
FIG. 4 is a graph of the lateral resolution of each embodibent.

FIG. 4 is a graph of lateral direction parallel to the Z-axis with respect to distance y from the transducer in each of the embodiments described above, and in the conventional transducer. $\Delta_1$ denotes the resolution when the conventional round transducer is used, $\Delta_2$ that when the elliptical transducer of FIGS. 2A and 2B is used, and $\Delta_3$ that when multi-stage focusing is provided using the multi-ring elliptical transducer of FIG. 3. As can be seen clearly from this graph, the resolution can be improved near the focus by the use of an elliptical transducer. Furthermore, the transducer of FIG. 3 provides an improved resolution over the entire zone. This means that the thickness of a tomograph section is reduced.

Although the invention has been described with reference to preferred embodiments thereof applied to a side-viewing echo endoscope which is inserted through the gullet, the invention can obviously be applied to the probe for transrectal tomography.

What is claimed is:

1. A probe for an intraluminal ultrasonic scanner comprising:
an acoustic case of substantially cylindrical shape having a center axis and arranged for insertion in a lumen of a patient, said acoustic case containing a liquid medium;
a rotary shaft disposed along the center axis of said acoustic case and arranged for coupling with a rotating means for rotating said rotary shaft;
an ultrasonic transducer positioned in said acoustic case and coupled to said rotary shaft so that said ultrasonic transducer transmits and receives ultrasonic beams in a direction substantially perpendicular to said center axis of said acoustic case, said ultrasonic transducer being coupled to said rotary shaft for being mechanically rotated about said center axis of said acoustic case, said acoustic transducer having a transducer surface with a length extending in a direction parallel to the center axis which is longer than the length of the transducer surface thereof extending perpendicular to the center axis.

2. A probe according to claim 1, wherein said transducer surface has an elliptical shape.

3. A probe according to claim 1, wherein said ultrasonic transducer is a concave ultrasonic transducer.

4. A probe according to claim 1, wherein said ultrasonic transducer comprises a plurality of ring-shaped members.

* * * * *